(12) United States Patent
Carlino et al.

(10) Patent No.: US 12,083,013 B2
(45) Date of Patent: Sep. 10, 2024

(54) BENDABLE CARDIAC SURGERY INSTRUMENTS

(71) Applicant: Corcym S.r.l., Milan (IT)

(72) Inventors: Felice Guiseppe Carlino, Borgomasino (IT); Monica Francesca Achiluzzi, Chivasso (IT)

(73) Assignee: CORCYM S.r.l., Saluggia (IT)

( * ) Notice: Subject to any disclaimer, the term of this patent is extended or adjusted under 35 U.S.C. 154(b) by 1192 days.

(21) Appl. No.: 16/754,309

(22) PCT Filed: Mar. 27, 2018

(86) PCT No.: PCT/IB2018/052064
§ 371 (c)(1),
(2) Date: Apr. 7, 2020

(87) PCT Pub. No.: WO2019/069145
PCT Pub. Date: Apr. 11, 2019

(65) Prior Publication Data
US 2020/0237510 A1    Jul. 30, 2020

Related U.S. Application Data

(60) Provisional application No. 62/569,509, filed on Oct. 7, 2017.

(51) Int. Cl.
*A61F 2/24* (2006.01)
*A61B 5/00* (2006.01)
(Continued)

(52) U.S. Cl.
CPC .......... *A61F 2/2427* (2013.01); *A61B 5/1076* (2013.01); *A61B 5/6852* (2013.01); *A61B 2505/05* (2013.01); *A61M 25/0054* (2013.01)

(58) Field of Classification Search
CPC ........ A61F 2/2427; A61F 2/2439; A61F 2/95; A61B 5/1076; A61B 5/6852
See application file for complete search history.

(56) References Cited

U.S. PATENT DOCUMENTS

| 3,363,442 A | 1/1968 | Kennedy et al. |
| 3,744,140 A | 7/1973 | Kyrk |
| (Continued) | | |

FOREIGN PATENT DOCUMENTS

| DE | 29911694 U1 | 8/1999 |
| DE | 102004019254 B8 | 11/2005 |
| (Continued) | | |

OTHER PUBLICATIONS

International Search Report & Written Opinion dated Jul. 13, 2018 in Int'l PCT Patent Application Serial No. PCT/IB2018/052064.

*Primary Examiner* — Christopher D. Prone
(74) *Attorney, Agent, or Firm* — Crowe & Dunlevy LLC

(57) ABSTRACT

A bendable medical instrument including: a handle at a proximal end of the bendable medical instrument, a modular distal shaft including a plurality of vertebrae configured to bend and situated near a distal end of the bendable medical instrument, a bendable internal rod disposed through at least some of the plurality of vertebrae, the bendable internal rod having a modular cell structure, and a distal tip coupled to the modular distal shaft at the distal end. The plurality of vertebrae configured to bend to position the distal tip in a patient and the bendable internal rod configured to bend with the plurality of vertebrae.

26 Claims, 10 Drawing Sheets

(51) Int. Cl.
*A61B 5/107* (2006.01)
*A61M 25/00* (2006.01)

(56) References Cited

U.S. PATENT DOCUMENTS

| | | |
|---|---|---|
| 5,042,161 A | 8/1991 | Hodge |
| 5,360,014 A | 11/1994 | Sauter et al. |
| 5,489,296 A | 2/1996 | Love et al. |
| 5,505,689 A | 4/1996 | Kramer et al. |
| 5,522,884 A | 6/1996 | Wright |
| 5,560,487 A | 10/1996 | Starr |
| 5,669,919 A | 9/1997 | Sanders et al. |
| 5,672,169 A | 9/1997 | Verbeek |
| 5,693,066 A | 12/1997 | Rupp et al. |
| 5,698,307 A | 12/1997 | Levy |
| 5,776,187 A | 7/1998 | Krueger et al. |
| 5,800,531 A | 9/1998 | Cosgrove et al. |
| 5,810,873 A | 9/1998 | Morales |
| 5,814,096 A | 9/1998 | Lam et al. |
| 5,814,098 A | 9/1998 | Hinnenkamp et al. |
| 5,885,031 A | 3/1999 | White |
| 5,885,228 A | 3/1999 | Rosenman et al. |
| 5,947,993 A | 9/1999 | Morales |
| 5,951,540 A | 9/1999 | Verbeek |
| 5,972,016 A | 10/1999 | Morales |
| 5,984,959 A | 11/1999 | Robertson et al. |
| 6,019,739 A | 2/2000 | Rhee et al. |
| 6,024,737 A | 2/2000 | Morales |
| 6,051,002 A | 4/2000 | Morales |
| 6,063,102 A | 5/2000 | Morales |
| 6,110,200 A | 8/2000 | Hinnenkamp |
| 6,202,272 B1 | 3/2001 | Jackson |
| 6,277,110 B1 | 8/2001 | Morales |
| 6,309,383 B1 | 10/2001 | Campbell et al. |
| 6,350,281 B1 | 2/2002 | Rhee |
| 6,352,547 B1 | 3/2002 | Brown et al. |
| 6,387,117 B1 | 5/2002 | Arnold, Jr. et al. |
| 6,402,780 B2 | 6/2002 | Williamson, IV et al. |
| 6,424,885 B1 | 7/2002 | Niemeyer et al. |
| 6,454,799 B1 | 9/2002 | Schreck |
| 6,481,262 B2 | 11/2002 | Ching et al. |
| 6,493,608 B1 | 12/2002 | Niemeyer |
| 6,506,201 B2 | 1/2003 | Di Caprio et al. |
| 6,510,722 B1 | 1/2003 | Ching et al. |
| 6,598,307 B2 | 7/2003 | Love et al. |
| 6,629,350 B2 | 10/2003 | Motsenbocker |
| 6,676,684 B1 | 1/2004 | Morley et al. |
| 6,678,962 B1 | 1/2004 | Love et al. |
| 6,726,713 B2 | 4/2004 | Schaldach et al. |
| 6,730,118 B2 | 5/2004 | Spenser et al. |
| 6,769,161 B2 | 8/2004 | Brown et al. |
| 6,846,324 B2 | 1/2005 | Stobie |
| 6,915,560 B2 | 7/2005 | Austin |
| 6,966,924 B2 | 11/2005 | Holmberg |
| 6,968,607 B2 | 11/2005 | Motsenbocker |
| 6,981,982 B2 | 1/2006 | Armstrong et al. |
| 6,988,881 B2 | 1/2006 | Motsenbocker et al. |
| 7,007,396 B2 | 3/2006 | Rudko et al. |
| 7,021,114 B2 | 4/2006 | Perreault |
| 7,069,794 B2 | 7/2006 | Motsenbocker et al. |
| 7,090,688 B2 | 8/2006 | Nishtala et al. |
| 7,258,698 B2 | 8/2007 | Lemmon |
| 7,338,484 B2 | 3/2008 | Schoon et al. |
| 7,357,814 B2 | 4/2008 | Gabbay |
| 7,367,984 B2 | 5/2008 | Kulcinski et al. |
| 7,427,291 B2 | 9/2008 | Liddicoat et al. |
| 7,453,227 B2 | 11/2008 | Prisco et al. |
| 7,455,690 B2 | 11/2008 | Cartledge et al. |
| 7,857,845 B2 | 12/2010 | Stacchino et al. |
| 8,006,535 B2 | 8/2011 | Righini et al. |
| 8,109,996 B2 | 2/2012 | Stacchino et al. |
| 8,177,794 B2* | 5/2012 | Cabrera ............ A61B 17/0491 606/144 |
| 8,376,865 B2* | 2/2013 | Forster .................. F16C 1/04 464/78 |
| 2001/0049558 A1 | 12/2001 | Liddicoat et al. |
| 2002/0035390 A1 | 3/2002 | Schaldach et al. |
| 2002/0042651 A1 | 4/2002 | Liddicoat et al. |
| 2002/0129820 A1 | 9/2002 | Ryan et al. |
| 2002/0198594 A1 | 12/2002 | Schreck |
| 2003/0114913 A1 | 6/2003 | Spenser et al. |
| 2003/0125805 A1 | 7/2003 | Johnson et al. |
| 2003/0192164 A1 | 10/2003 | Austin |
| 2004/0039436 A1 | 2/2004 | Spenser et al. |
| 2004/0123437 A1 | 7/2004 | Kokish |
| 2004/0193259 A1 | 9/2004 | Gabbay |
| 2004/0225356 A1 | 11/2004 | Frater |
| 2005/0166389 A1 | 8/2005 | Perreault et al. |
| 2005/0197695 A1 | 9/2005 | Stacchino et al. |
| 2005/0197696 A1 | 9/2005 | Gomez Duran |
| 2005/0229670 A1 | 10/2005 | Perreault |
| 2005/0234537 A1 | 10/2005 | Edin |
| 2005/0240256 A1 | 10/2005 | Austin |
| 2005/0267529 A1 | 12/2005 | Crockett et al. |
| 2005/0283232 A1 | 12/2005 | Gabbay |
| 2006/0004469 A1 | 1/2006 | Sokel |
| 2006/0074486 A1 | 4/2006 | Liddicoat et al. |
| 2006/0178740 A1 | 8/2006 | Stacchino et al. |
| 2006/0265855 A1 | 11/2006 | Stenzel |
| 2007/0027534 A1 | 2/2007 | Bergheim et al. |
| 2007/0056346 A1 | 3/2007 | Spenser et al. |
| 2007/0061009 A1 | 3/2007 | Spenser et al. |
| 2007/0100356 A1 | 5/2007 | Lucatero et al. |
| 2007/0151116 A1 | 7/2007 | Malandain |
| 2007/0162113 A1 | 7/2007 | Sharkawy et al. |
| 2007/0173861 A1 | 7/2007 | Strommer et al. |
| 2008/0147076 A1 | 6/2008 | Geisert et al. |
| 2008/0147160 A1 | 6/2008 | Ghione et al. |
| 2008/0147182 A1 | 6/2008 | Righini et al. |
| 2008/0262603 A1 | 10/2008 | Giaquinta et al. |
| 2008/0281232 A1 | 11/2008 | Lansac et al. |
| 2009/0018570 A1 | 1/2009 | Righini et al. |
| 2009/0069886 A1 | 3/2009 | Suri et al. |
| 2009/0069887 A1 | 3/2009 | Righini et al. |
| 2009/0099653 A1 | 4/2009 | Suri et al. |
| 2009/0192602 A1 | 7/2009 | Kuehn |
| 2009/0192603 A1 | 7/2009 | Ryan |
| 2009/0287296 A1 | 11/2009 | Manasse |
| 2010/0160832 A1 | 6/2010 | Braido |
| 2010/0249661 A1* | 9/2010 | Righini ................ A61B 5/1076 606/198 |
| 2010/0262043 A1 | 10/2010 | Sauter et al. |
| 2014/0166718 A1 | 6/2014 | Swayze et al. |
| 2014/0207011 A1 | 7/2014 | Righini et al. |
| 2014/0243592 A1* | 8/2014 | Kato ................ A61B 17/00234 600/141 |
| 2017/0156866 A1 | 6/2017 | Righini et al. |

FOREIGN PATENT DOCUMENTS

| | | |
|---|---|---|
| DE | 202011000848 U1 | 6/2011 |
| EP | 0095970 A2 | 12/1983 |
| EP | 0778009 B1 | 7/2002 |
| EP | 1353420 B1 | 3/2005 |
| EP | 3034014 A2 | 6/2016 |
| GB | 2083362 A | 3/1982 |
| JP | H11332997 A | 12/1999 |
| JP | 2004154164 A | 6/2004 |
| WO | WO-9639942 A1 | 12/1996 |
| WO | WO-9724989 A1 | 7/1997 |
| WO | WO-9814138 A1 | 4/1998 |
| WO | WO-9953864 A1 | 10/1999 |
| WO | WO-9953866 A1 | 10/1999 |
| WO | WO-9955255 A1 | 11/1999 |
| WO | WO-0006052 A1 | 2/2000 |
| WO | WO-0021464 A1 | 4/2000 |
| WO | WO-0030565 A1 | 6/2000 |
| WO | WO-0121076 A1 | 3/2001 |
| WO | WO-0121097 A2 | 3/2001 |
| WO | WO-0121110 A1 | 3/2001 |
| WO | WO-0176510 A2 | 10/2001 |
| WO | WO-0211646 A1 | 2/2002 |
| WO | WO-0121110 A9 | 8/2002 |
| WO | WO-0121103 A9 | 10/2002 |

(56) References Cited

FOREIGN PATENT DOCUMENTS

| | | |
|---|---|---|
| WO | WO-02092257 A1 | 11/2002 |
| WO | WO-2005082578 A1 | 9/2005 |
| WO | WO-2006007401 A2 | 1/2006 |
| WO | WO-2006088712 A1 | 8/2006 |
| WO | WO-2006117016 A1 | 11/2006 |
| WO | WO-2006127089 A1 | 11/2006 |
| WO | WO-2006136930 A1 | 12/2006 |
| WO | WO-2007030825 A3 | 6/2007 |
| WO | WO-2006007401 A3 | 1/2008 |
| WO | WO-0121097 A3 | 3/2008 |
| WO | WO-2008089365 A2 | 7/2008 |
| WO | WO-2010112608 A1 | 10/2010 |

* cited by examiner

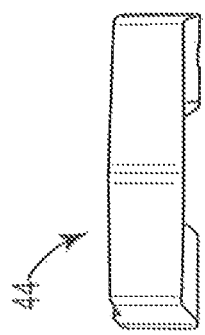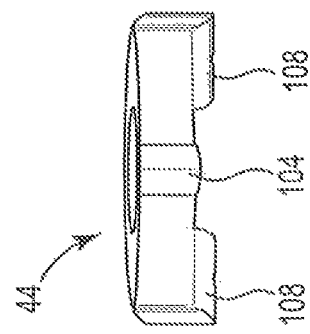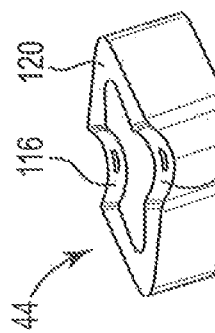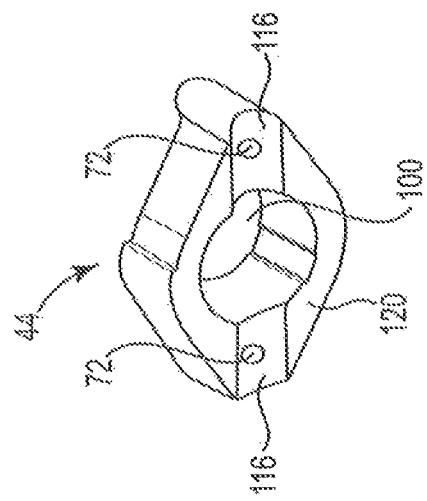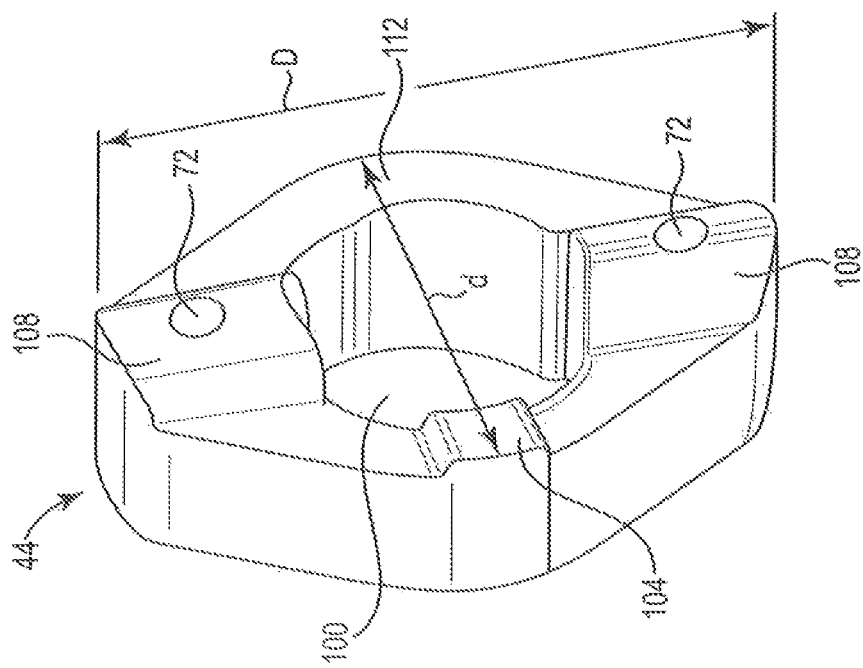

BENDABLE CARDIAC SURGERY INSTRUMENTS

CROSS-REFERENCE TO RELATED APPLICATION

This application is a national stage application of PCT/IB2018/052064, filed Mar. 27, 2018, which claims priority to Provisional Application No. 62/569,509, filed Oct. 7, 2017, which is herein incorporated by reference in its entirety.

TECHNICAL FIELD

This disclosure is related to cardiac surgery instruments and, more particularly, to minimally invasive cardiac surgery instruments.

BACKGROUND

In some heart patients, a native heart valve needs to be replaced and/or repaired with a prosthetic heart valve. Medical researchers have found that the efficiency of the prosthetic heart valve is dependent on the size of the valve, where improved hemodynamic characteristics can be expected if the size of the central orifice of the prosthetic heart valve is similar to the size of the central orifice of the patient's native heart valve. Thus, heart valve sizing, such as by using a heart valve sizer, is important for minimizing the risk of inaccurately sizing the prosthetic heart valve and assuring that the prosthetic heart valve properly fits the patient. In addition, at least some prosthetic heart valves, such as expandable prosthetic heart valves, perform better if aligned with the central axis of the native heart valve.

Medical personnel utilize a number of different techniques for replacing and/or repairing native heart valves in patients. Some of these techniques include minimally invasive thoracic access procedures, such as mini-thoracotomy and mini-sternotomy procedures. One drawback of minimally invasive thoracic access procedures is the lack of space for positioning devices, such as heart valve sizing and heart valve delivery devices. Often, in these procedures, positioning the devices in relation to the autogenous tissue may be difficult. Where, in the majority of cases, this lack of space results in an angle, such as an acute angle, between the inserted instrument and a central axis of the native heart valve, which can make heart valve sizing and prosthetic heart valve delivery or implantation difficult and, in some cases, even impossible.

SUMMARY

The present disclosure describes systems including instruments and methods, which overcome the difficulties associated with accessing a native heart valve in a patient. Embodiments of the instruments include an elongated shaft to extend over long distances per minimally invasive cardiac surgery (MICS) and a modular distal shaft that is similar to a spinal column situated near the distal end of the elongated shaft. The modular distal shaft is bendable and provides easy passage through an incision in the patient's chest to the native heart valve. The modular distal shaft is selectively bendable to provide a curved shape and to vary the spatial orientation of the distal end of the instrument with respect to the native heart valve, which allows for proper alignment of the instrument to the native heart valve, including the axis of the native heart valve. Also, the modular distal shaft is manually bendable and configured to retain the shape into which it is bent.

As recited in examples, example 1 is a bendable medical instrument including a handle at a proximal end of the bendable medical instrument, a modular distal shaft including a plurality of vertebrae configured to bend and situated near a distal end of the bendable medical instrument, a bendable internal rod disposed through at least some of the plurality of vertebrae, the bendable internal rod having a modular cell structure, and a distal tip coupled to the modular distal shaft at the distal end, wherein the plurality of vertebrae are configured to bend to position the distal tip in a patient and the bendable internal rod is configured to bend with the plurality of vertebrae.

Example 2 is the instrument of example 1, including at least one guide wire coupled to at least one of the handle and the modular distal shaft and operatively coupled to the plurality of vertebrae.

Example 3 is the instrument of example 1, wherein each of the plurality of vertebrae has at least one guide hole configured to allow a guide wire to extend through the guide hole.

Example 4 is the instrument of example 1, wherein the handle comprises a deployable component control knob configured to control a deployable component at the distal end.

Example 5 is the instrument of example 1, wherein the distal tip comprises a deployable component and the handle comprises a deployable component control knob configured to provide at least one of control over a degree of deployment of the deployable component and measuring of the degree of deployment of the deployable component.

Example 6 is the instrument of example 1, wherein the bendable internal rod is configured to transmit torque from the proximal end to the distal end.

Example 7 is the instrument of example 6, wherein the bendable internal rod has a swallowtail cell structure.

Example 8 is the instrument of example 1, wherein the bendable internal rod is bendable in four directions.

Example 9 is the instrument of example 1, wherein each of the plurality of vertebrae defines a central hole configured to allow the bendable internal rod to extend through the central hole.

Example 10 is the instrument of example 1, wherein the modular distal shaft is bendable in four directions.

Example 11 is the instrument of example 1, wherein each of the plurality of vertebrae has a blocking protrusion configured to disable relative rotational movement between the plurality of vertebrae.

Example 12 is the instrument of example 1, wherein each of the plurality of vertebrae has at least one alignment protrusion on a front side and at least one alignment groove on a back side to couple and align the plurality of vertebrae into the modular distal shaft.

Example 13 is the instrument of example 1, wherein each vertebra has two guide holes configured to allow a guide wire to extend through the guide hole, wherein each guidewire is plastically deformable and configured to maintain the shape imparted thereto upon deformation.

Example 14 is the instrument of example 13, wherein each guidewire includes a first end and a second end fixed, respectively, to a first terminal member and a second terminal member arranged at opposite ends of the plurality of vertebrae.

Example 15 is the instrument of example 14, wherein the first end and the second end of each guidewire are curved or otherwise bent.

Example 16 is the instrument of any of examples 13 to 15, wherein each vertebra has a rhomboidal shape including a major dimension and a minor dimension, wherein the two guide holes are arranged along the major dimension.

Example 17 is the instrument of example 5, wherein the deployable component includes a valve annulus sizing device comprising:
 a holder having a proximal end and a distal end, the proximal end of the holder being coupled to the modular distal shaft,
 a hub member rotationally coupled to the bendable internal rod and rotatably mounted into a central chamber of the holder,
 a measuring band having a proximal end and a distal end, the proximal end being coupled to the holder, and the distal end being coupled to the hub member,
wherein the measuring band is wound about the holder and extends through a slot of the holder to the hub member.

Example 18 is the instrument of example 17, wherein the measuring band includes:
 a collapsed configuration wherein it is wound about the holder such that it extends along an outer surface of the holder, extends through the slot, and along an internal surface of the holder in the central chamber, and
 an expanded configuration wherein the measuring band is at least partially unwound to extend out through the slot and away from the holder.

Example 19 is a bendable medical instrument including a handle at a proximal end of the bendable medical instrument, a modular distal shaft situated near a distal end of the bendable medical instrument, the modular distal shaft including a plurality of vertebrae axially aligned and configured to provide bendability to the modular distal shaft, each of the plurality of vertebrae having at least one guide hole, at least one guide wire coupled to the handle and inserted through the at least one guide hole in each of the plurality of vertebrae, a rod including a plurality of cells axially aligned and configured to provide bendability to the rod, the rod coupled to the handle and disposed through each of the plurality of vertebrae, and a distal tip coupled to the modular distal shaft at the distal end, wherein the plurality of vertebrae are configured to bend and the rod is configured to bend inside the plurality of vertebrae.

Example 20 is the instrument of example 19, wherein the handle comprises a deployable component control knob configured to control a deployable component at the distal end.

Example 21 is the instrument of example 19, wherein each of the plurality of cells has a swallowtail cell structure.

Example 22 is the instrument of example 19, wherein the distal tip includes a deployable component coupled to the rod, and the handle includes a deployable component control knob coupled to the rod to control deployment of the deployable component.

Example 23 is a method of manipulating the position of a deployable component situated at a distal end of a bendable medical instrument, the method comprising bending a plurality of vertebrae in a modular distal shaft that is coupled to the deployable component and situated near the deployable component, each of the plurality of vertebrae having at least one guide hole and at least one guide wire inserted through the at least one guide hole, and bending a plurality of cells in a bendable internal rod coupled to the handle and disposed through each of the plurality of vertebrae.

Example 24 is the method of example 23, wherein bending a plurality of vertebrae and bending a plurality of cells comprises simultaneously bending the plurality of vertebrae and the plurality of cells.

Example 25 is the method of example 23, wherein bending a plurality of vertebrae comprises manually bending the plurality of vertebrae.

Example 26 is the method of example 23, wherein bending a plurality of cells comprises manually bending the plurality of cells.

BRIEF DESCRIPTION OF THE DRAWINGS

FIG. 5A is a diagram illustrating a vertebra of the modular distal shaft, in accordance with various embodiments of the disclosure.

FIG. 5B is a diagram illustrating the vertebra of the modular distal shaft, in accordance with various embodiments of the disclosure.

FIG. 5C is a diagram illustrating the vertebra of the modular distal shaft, in accordance with various embodiments of the disclosure.

FIG. 5D is a diagram illustrating the vertebra of the modular distal shaft, in accordance with various embodiments of the disclosure.

FIG. 5E is a diagram illustrating the vertebra of the modular distal shaft, in accordance with various embodiments of the disclosure.

Figure 1:
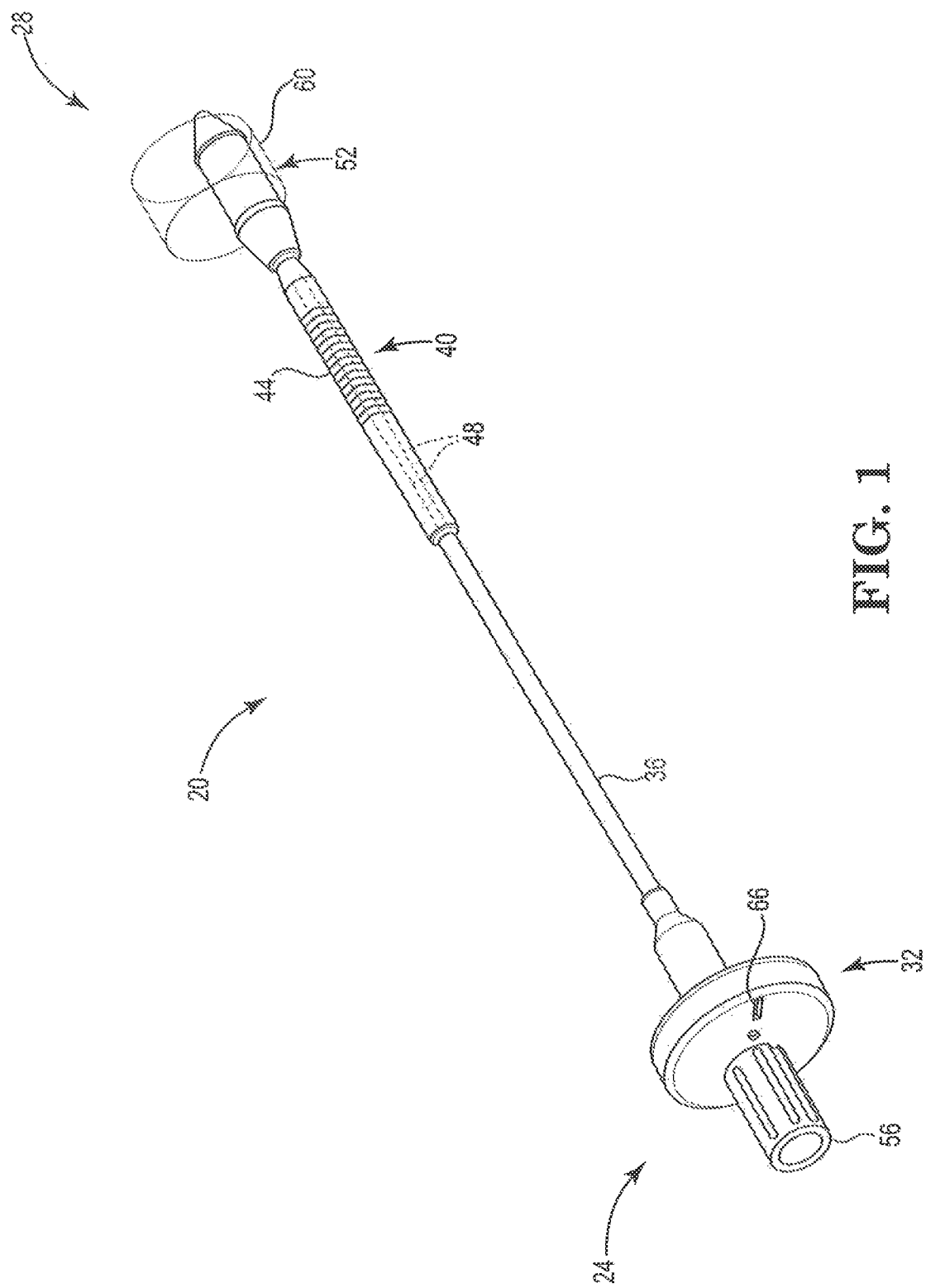
FIG. 1 is a diagram illustrating a bendable MICS instrument in a neutral state, in accordance with various embodiments of the disclosure.

While the disclosure is amenable to various modifications and alternative forms, embodiments have been shown by way of example in the drawings and are described in detail below. The intention, however, is not to limit the disclosure to the embodiments described. On the contrary, the disclosure is intended to cover all modifications, equivalents, and alternatives falling within the scope of the disclosure as defined by the appended claims.

DETAILED DESCRIPTION

FIG. 1 is a diagram illustrating a bendable MICS instrument 20 in a neutral state, in accordance with various embodiments of the disclosure. The bendable MICS instrument 20 comprises a proximal end 24, a distal end 28, a handle 32 at the proximal end 24, an elongated extension shaft 36 coupled to the handle 32, and a modular distal shaft 40 coupled to the extension shaft 36 and situated near the distal end 28. The modular distal shaft 40 includes a plurality of vertebrae 44, a bendable internal rod 48 disposed inside the modular distal shaft 40, and a distal tip 52 coupled to the modular distal shaft 40 at the distal end 28. In the neutral state, the extension shaft 36 and the modular distal shaft 40 are substantially coaxial.

The handle 32 includes a deployable component control knob or mechanism 56 configured to control a deployable component 60 at the distal end 28. The extension shaft 36 and the modular distal shaft 40 are long enough to reach a site of interest in the patient using different surgical procedures, including MICS. In some embodiments, each of the extension shaft 36 and the modular distal shaft 40 is about 100 mm or longer. For example, in one embodiment the extension shaft is 120 mm long and the modular distal shaft is 100 mm long, while the distal tip is 50 mm long, and the handle 32 is 90 mm long. More in general, the following dimension ranges may be considered as representative of embodiments herein: extension shaft 100 to 120 mm; modular distal shaft 80 to 100 mm; distal tip 40 to 60 mm; and handle 80 to 110 mm.

In some embodiments, the distal tip 52 includes the deployable component 60, such as an expandable valve annulus sizing device as depicted in FIG. 1. In other embodiments, the deployable component 60 can include an expandable valve holder, a valve delivery instrument, a balloon, a sensor, a detector, an ablation tool, and an electrode. In some embodiments, the deployable component control knob 56 is configured to control and/or measure a degree of deployment of the deployable component 60.

In some embodiments, the instrument 20 includes the deployable component 60 and is similar to devices described in U.S. application Ser. No. 15/433,970, filed Feb. 15, 2017, entitled "UNIVERSAL VALVE ANNULUS SIZING DEVICE," and published as U.S. Publication No. 2017/0156866, which are all herein incorporated by reference in their entirety.

In some embodiments, the instrument 20 includes the deployable component 60 and is similar to devices described in U.S. application Ser. No. 12/727,098, filed Mar. 18, 2010, entitled "UNIVERSAL VALVE ANNULUS SIZING DEVICE," now U.S. Pat. No. 8,715,207, which are all herein incorporated by reference in their entirety.

Figure 2:
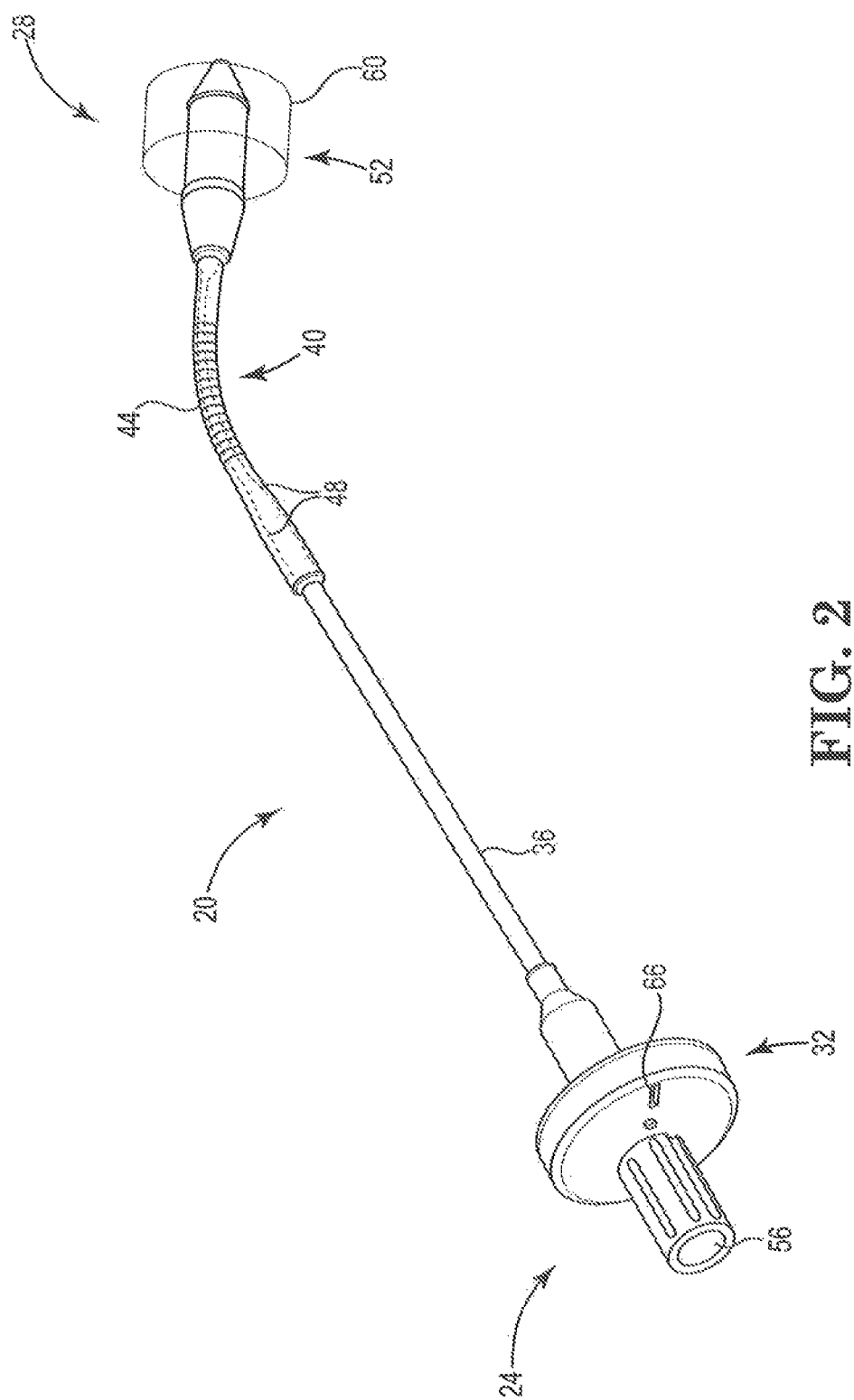
FIG. 2 is a diagram illustrating the bendable MICS instrument in a bent state, in accordance with various embodiments of the disclosure.

FIG. 2 is a diagram illustrating the bendable MICS instrument 20 in a bent state, in accordance with various embodiments of the disclosure. In the bent state, the extension shaft 36 and the modular distal shaft 40 are not coaxial. In some embodiments, the modular distal shaft 40 is bendable in at least one direction (generally on a plane). In some embodiments, the modular distal shaft 40 is bendable in two to four directions (generally on orthogonal planes, when four).

The deployable component control knob 56 can be one of a dial, a slider, a plurality of preset buttons, a pressure-sensitive button, a trigger, a spreader, or any other suitable control mechanism. As shown in FIG. 2, the handle 32 includes a status indicator 66 for indicating at least one of the percentage or degree of deployment of the deployable component 60, or a detected annulus/valve size in case the deployable component is embodied by the annulus sizing device referred to above.

Figure 3:
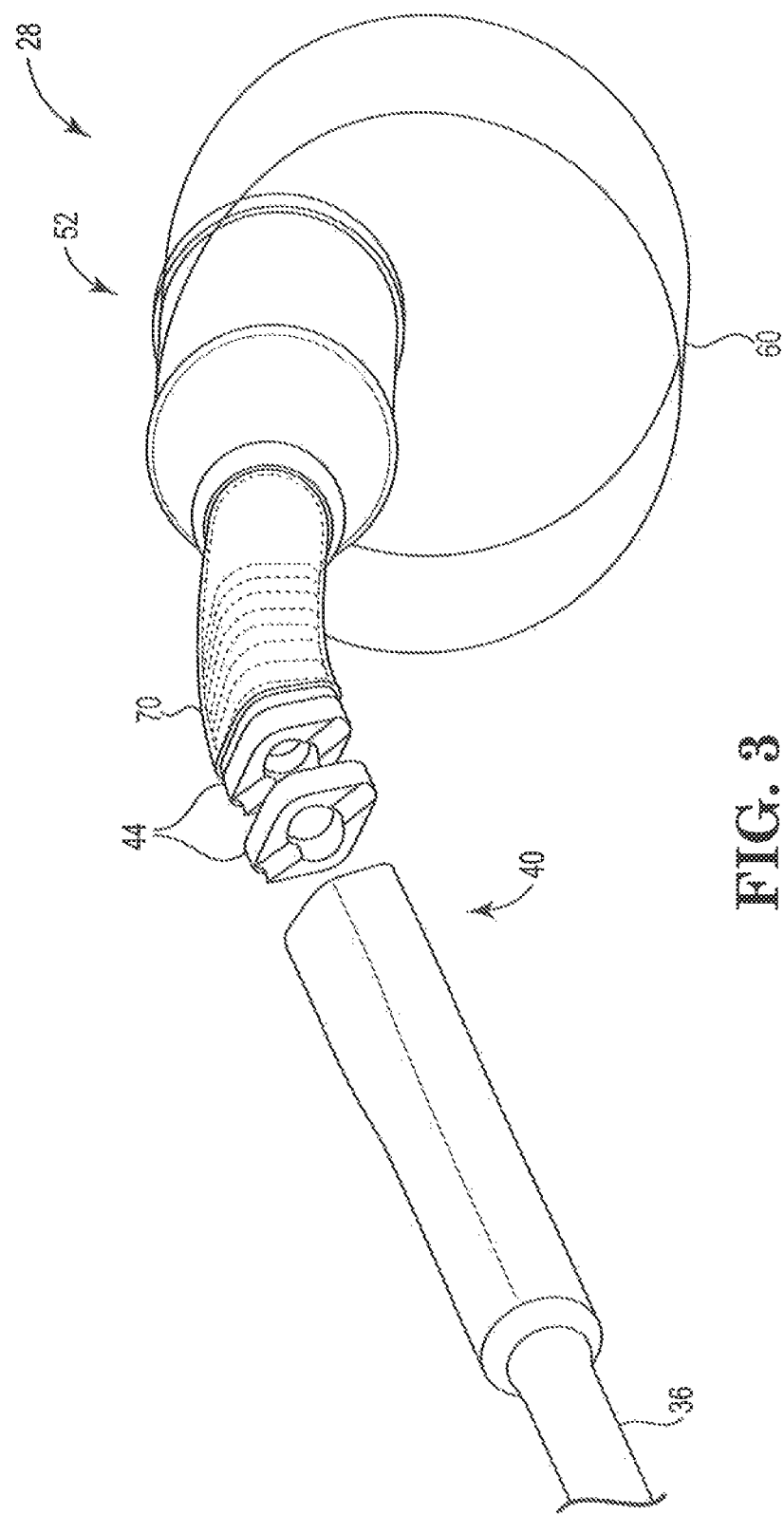
FIG. 3 is a diagram illustrating a modular distal shaft of the bendable MICS instrument, in accordance with various embodiments of the disclosure.

FIG. 3 is a diagram illustrating the modular distal shaft 40 of the bendable MICS instrument 20, in accordance with various embodiments of the disclosure. The modular distal shaft 40 includes the plurality of vertebrae 44 coupled together consecutively, similar to a spinal column. In some embodiments, each of the plurality of vertebrae 44 is one of metallic and polymeric. In some embodiments, the modular distal shaft 40 includes a flexible housing or cover 70 that covers the plurality of vertebrae 44. In some embodiments, the flexible housing 70 includes plastic and/or a polymer.

Figure 4A:
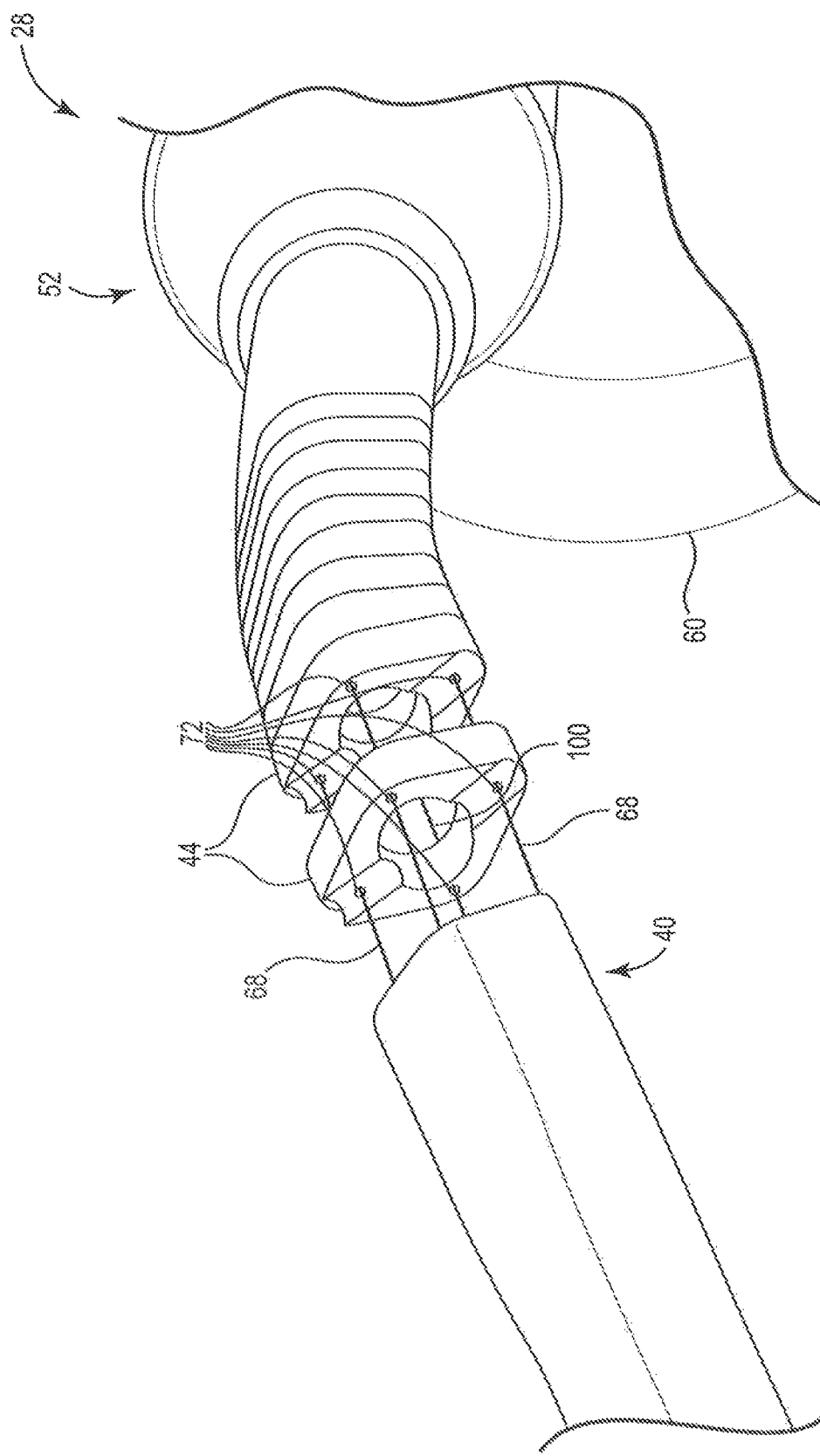
FIG. 4A is a diagram illustrating the modular distal shaft with guide wires, in accordance with various embodiments of the disclosure.

FIG. 4A is a diagram illustrating the modular distal shaft 40 including stabilization wires or guide wires 68, in accordance with various embodiments of the disclosure. The bendable MICS instrument 20 includes at least one guide wire 68 operatively coupled to or through the plurality of vertebrae 44. The stabilization wires or guide wires 68 can be anchored at a suitable location, such as toward the proximal end 24 in at least one of the handle 32, the extension shaft 36, and the modular distal shaft 40, and guided through the vertebrae 44 and anchored toward the distal end 28, such as at the distal portion of the vertebrae 44 or at the distal tip 52. The stabilization wires or guide wires 68 apply a tension force that holds the vertebrae 44 together and creates a friction force between the vertebrae 44. The modular distal shaft 40 is manually manipulated or bent to bend the modular distal shaft 40 at the vertebrae 44, such that the tension force and the friction force maintain the modular distal shaft 40 in the position into which it is bent. Each of the plurality of vertebrae 44 includes at least one guide hole 72 configured to allow one guide wire 68 to extend through the guide hole 72, where each of the guide holes 72 on one vertebra 44 is aligned with a corresponding guide hole 72 on an adjacent vertebra 44. In some embodiments, each of the guide wires 68 has a first end coupled to the handle 32 and a second end coupled near the distal end 28 of the bendable MICS instrument 20.

As illustrated in FIG. 4A, each of the plurality of vertebrae 44 includes four guide holes 72 that are aligned with four guide holes 72 in adjacent vertebrae 44. One of four guide wires 68 extends through each of the corresponding guide holes 72, where, in some embodiments, each of the guide wires 68 has a first end coupled to the handle 32 and a second end coupled near the distal end 28 of bendable MICS instrument 20. In some embodiments, the four wires 68 are disposed 90 degrees from each other. In some embodiments, the bendable MICS instrument 20 includes two wires 68 disposed 180 degrees from each other.

In some embodiments, at least one of the guide wires 68 is a spring attached to the handle 32 near the proximal end 24 and to the distal tip 52 near the distal end 28. In some embodiments, each of the guide wires includes one of metallic and polymeric materials.

In some embodiments, the modular distal shaft 40 is manually bent external to or outside the patient's body and through plastic deformation of the guide wires 68 (passive bending). In other embodiments, the modular distal shaft 40 is bent while it is inside the patient's body.

Figure 4B:
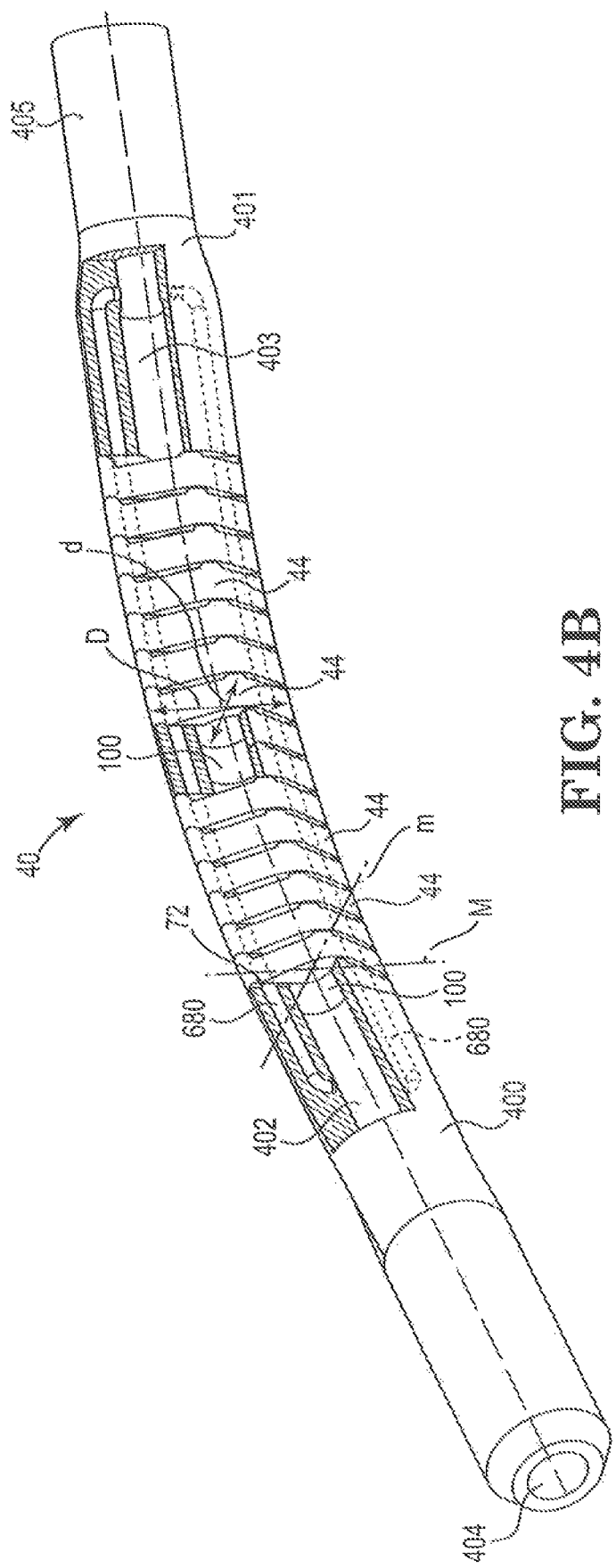
FIG. 4B is a diagram, partly sectioned, illustrating the modular distal shaft, in accordance with various embodiments of the disclosure

Embodiments are depicted in FIG. 4B, which corresponds to a partial sectional view of the modular distal shaft 40. Each of the plurality of vertebrae 44 includes two guide holes 72 that are aligned with two guide holes 72 in adjacent vertebrae 44. In these and other embodiments, each of the vertebrae 44 has a substantially rhomboidal shape that includes a major dimension D and minor dimension d (FIG. 4B, 5A), each of these dimensions being measured along a respective direction, both vertex-to-vertex direction, wherein a "major" direction is identified by reference M in FIG. 4B, while a "minor" direction is identified by reference m in FIG. 4B, each direction being orthogonal to one another. The guide holes 72 are preferably aligned along the major dimension direction, as visible in FIG. 4B. However, alignment along the minor dimension direction may be envisaged alternatively to the major dimension. In any case, guide hole spacing is 180 degrees. Two guide wires 680 extend through each of the corresponding guide holes 72. In these embodiments, the guide wires 680 are provided as plastically deformable cores fixed at opposite ends of the plurality of vertebrae 44 at corresponding anchoring seats provided into a first terminal member 400 and a second terminal member 401 of the modular distal shaft arranged at opposite ends of the sequence of vertebrae 44.

The guide wires 680 may each have a curved end (e.g. hook-like or elbow-like, with a 90 degrees bend) to enhance anchoring of the same into the terminal members 400, 401. To this end, the seats provided in the terminal members for receiving the ends of the guide wires 680 may be shaped accordingly, i.e. they may exhibit a rectilinear portion follower by a curved or otherwise bent section at an end of the rectilinear portion to accommodate the end of the respective guide wires. Each of the terminal members 400, 401 is traversed by a respective central through hole 402, 403 and includes—at an end thereof—a hub portion 404, 405 which is configured for mating, respectively, with the extension shaft 36 and with the deployable component 52. In one of these embodiment, the terminal members 401, 402 are identical to one another. In another of these embodiments, the terminal members 401, 402 may be different from one another particularly in the axial length of the hub portion 404, 405 to possibly cope with different mating requirements depending on what the hub is intended for mating to. For example, the hub portion 404 may be longer than the hub portion 405 to provide a more stable coupling with the extension shaft 36.

The guide wires 680 are configured to be plastically deformed by manual outside action and keep the shape imparted upon deformation thereof. The material of the guide wires 680 is not only capable of accepting plastic deformations and maintaining the shape imparted following the same deformation, it is also capable of withstanding subsequent deformations (including those restoring the original shape thereof, generally straight) leading to a change in the imparted position. The guide wires 680 essentially act as a deformable structural core member for the vertebrae 44, which are thus displaced (resulting ultimately in a bending of the modular distal shaft 40) to follow or otherwise be arranged according to the shape imparted to the guide wires 680.

In these embodiments, bending of the modular distal shaft 40 is thus effected by positive action directly on the modular distal shaft itself, rather than "remotely" via the handle or other manipulation facility. Due to the properties of the guide wires 680, the modular distal shaft of these embodiments is essentially "self-locking" such that it requires no further action to keep the shape it is bent into. Bending of the modular distal shaft is primarily allowed in a plane in opposing directions. This plane belonging to the minor direction m/minor dimension d of the vertebrae and orthogonal to the major direction M/major dimension D (bending moment, considered as a vector, aligned with direction M). Equivalently, bending is allowed primarily in those directions wherein both guide wires 680 lie in a neutral position (e.g. like a sort of neutral axis) relative to the deformation being imparted, where neither guide wire 680 lies on an extrados or an intrados of the sequence of vertebrae 44. Deformation of the modular distal shaft along planes angularly offset from the above plane, while not in principle prevented by structural or geometric features, is generally resisted or discouraged in these embodiments due to deformation of the guide wires 680 outside of the neutral position. This is due to the inherent properties of the guide wires 680 and structural arrangement of the modular distal shaft where the guide wires 680 exhibit a substantial flexural stiffness, further increased by the structural configuration of the sequence of vertebrae 44. The resistance is a maximum where bending is effected on a plane belonging to the major direction M/major dimension D and orthogonal to the minor direction m/minor dimension d (bending moment, considered as a vector, aligned with direction m).

Each of FIG. 5A-FIG. 5E is a diagram illustrating one of the plurality of vertebrae 44 of the modular distal shaft 40, in accordance with various embodiments of the disclosure. Each of the plurality of vertebrae 44 defines a central hole 100 configured to allow at least the bendable internal rod 48 to extend through the central hole 100. Also, each of the plurality of vertebrae 44 has at least one alignment protrusion 108 on a front side 112 and at least one alignment groove 116 on a back side 120. The alignment protrusion 108 and alignment groove 116 are used to couple and align the plurality of vertebrae 44 into the modular distal shaft 40 in consecutive order.

With the plurality of vertebrae 44 aligned, the central holes 100 of adjacent vertebrae 44 (and, where applicable, the through holes 402, 403 on the terminal members 400, 401—which are preferentially made as having the same diameter as the holes 100) align such that the bendable internal rod 48 can be passed through the central holes 100, and the guide holes 72 of adjacent vertebrae 44 are aligned such that guide wires 68 or 680 can be passed through the guide holes 72. Also, as shown in FIG. 5A-FIG. 5C, each of the plurality of vertebrae 44 includes two guide holes 72. However, in other embodiments, each of the plurality of vertebrae 44 can have more than two guide holes 72, such as four guide holes 72. In addition, as shown in FIG. 5A, in some embodiments, each of the plurality of vertebrae 44 has a blocking protrusion 104 configured to engage a corresponding slot on an adjacent vertebra 44 to disable relative rotational movement between the plurality of vertebrae 44 or to limit bending to a certain direction.

Figure 6:
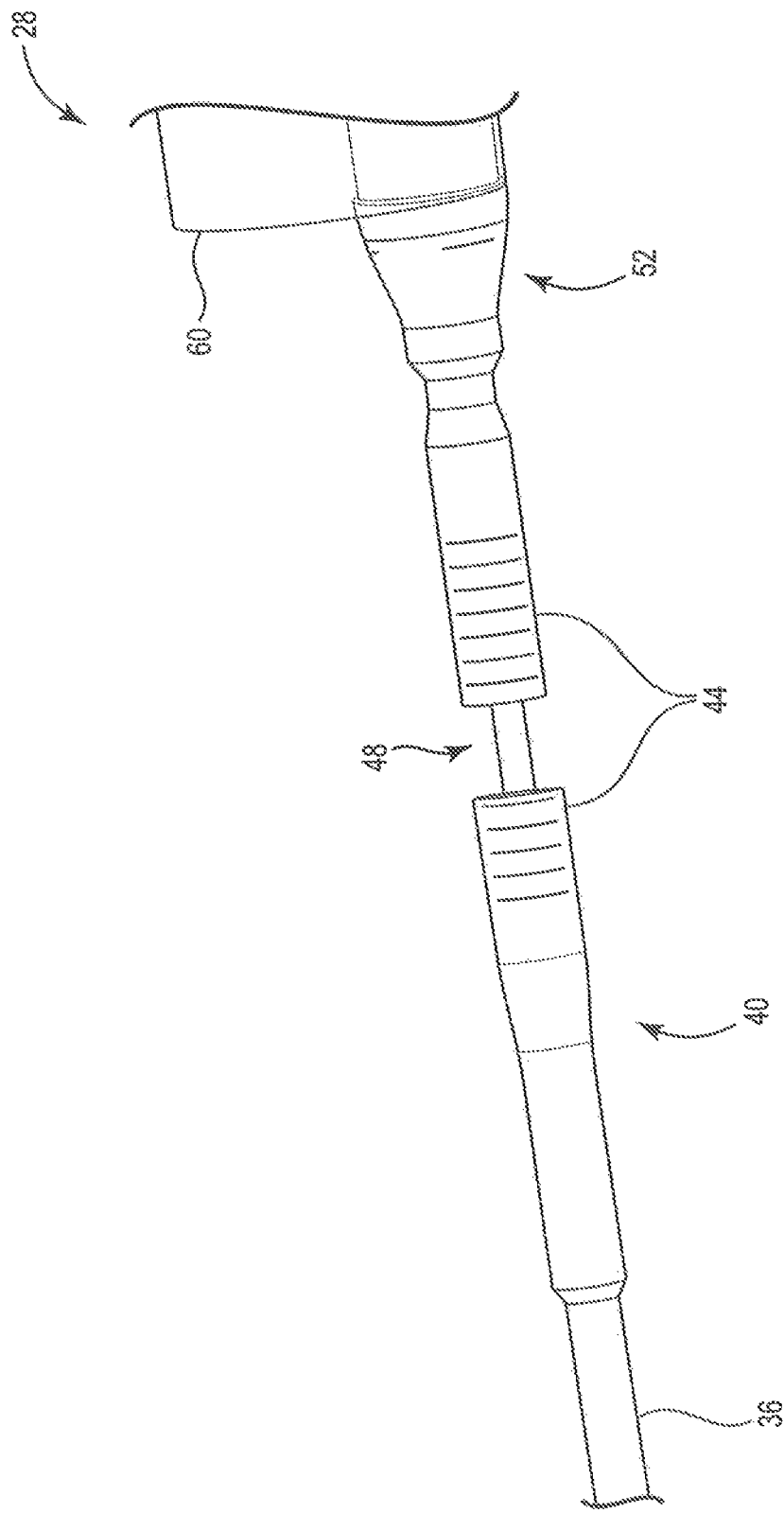
FIG. 6 is a diagram illustrating a bendable internal rod of the bendable MICS instrument, in accordance with various embodiments of the disclosure.

FIG. 6 is a diagram illustrating the bendable internal rod 48 of the bendable MICS instrument 20, in accordance with various embodiments of the disclosure. A section of the modular distal shaft 40 is shown without vertebrae 44 to show the bendable internal rod 48 disposed in the modular distal shaft 40. The bendable internal rod 48 is inserted through the central holes 100 of the plurality of vertebrae 44.

The bendable internal rod 48 can be coupled at the proximal end 24 to the handle 32 and at the distal end 28 to the deployable component 60. The bendable internal rod 48 is configured to transmit torque from the proximal end 24 to the distal end 28 of the instrument 20, such as to the deployable component 60. In some embodiments, the bendable internal rod 48 is configured to bend in four directions with a maximum degree of bending of 90 degrees.

Figure 7A:
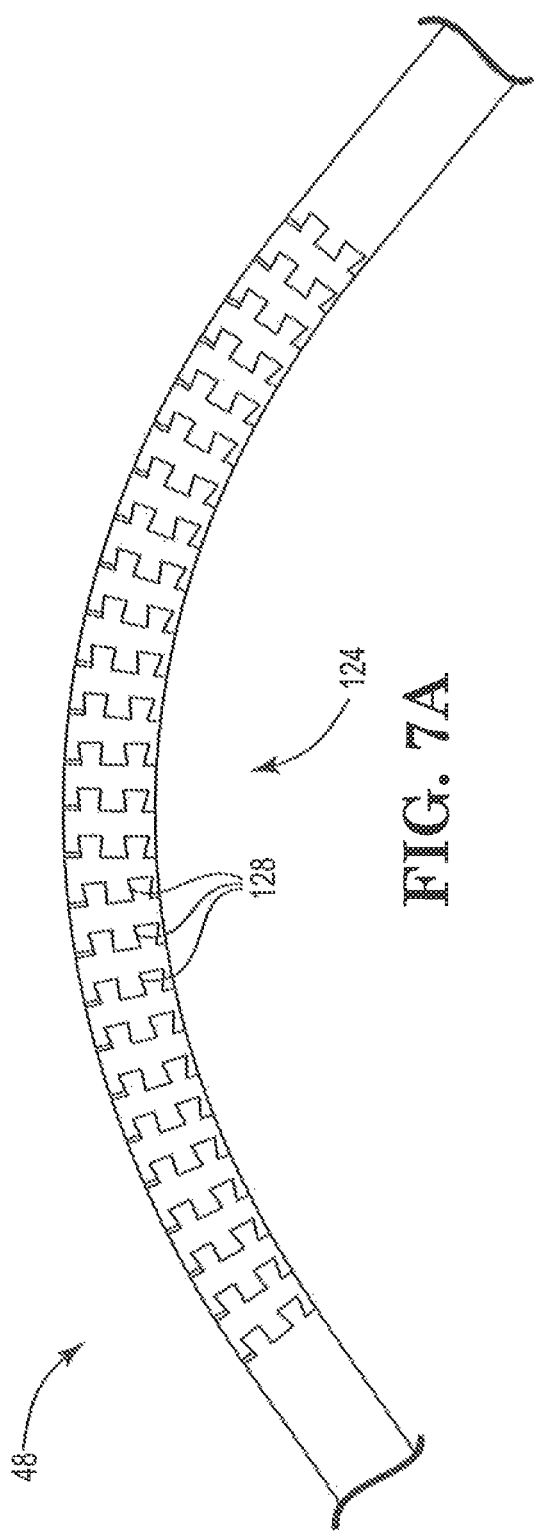
FIG. 7A is a diagram illustrating the bendable internal rod having a modular cell structure, in accordance with various embodiments of the disclosure.

FIG. 7A is a diagram illustrating the bendable internal rod 48 having a modular cell structure 124, in accordance with various embodiments of the disclosure. The modular cell structure 124 has a swallowtail cell structure that allows the bendable internal rod 48 to be bent and provide torque transmission from the proximal end 24 to the distal end 28. In various of the above embodiments, the bendable rod 48 is made by laser cutting the swallowtail pattern on the surface of a metal tube.

Figure 7B:
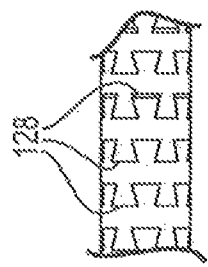
FIG. 7B is a diagram illustrating the swallowtail cell structure of the bendable internal rod, in accordance with various embodiments of the disclosure.

FIG. 7B is a diagram illustrating the swallowtail cell structure 124, in accordance with various embodiments of the disclosure. The cutout lines 128 represent where material is removed to allow bending of the bendable internal rod 48. Also, as illustrated in FIG. 7A, the swallow tail cell structure 124 squeezes together on the bottom portion and expands on the top portion of the curve to allow bending of the bendable internal rod 48.

In embodiments wherein the deployable component includes the valve annulus sizing device, the bendable internal rod 48 may allow the practitioner to control the degree of deployment of a measuring band of the device, which is shown in FIGS. 8 to 11.

Figure 8:
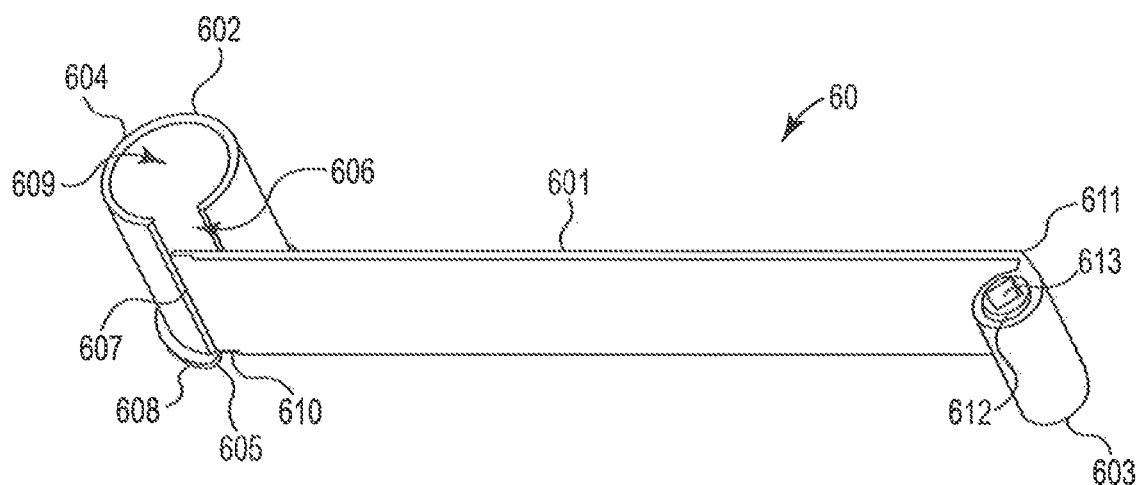
FIG. 8 is a diagram illustrating a sizing device partially disassembled, in accordance with various embodiments of the disclosure.
Figure 9:
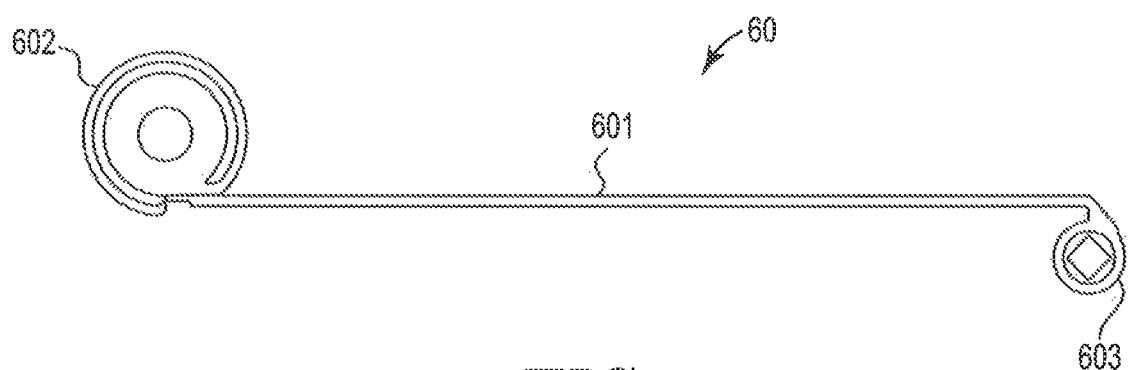
FIG. 9 is a diagram illustrating a side view of the sizing device partially disassembled, in accordance with various embodiments of the disclosure.

In the configuration shown in FIGS. 8, 9, for purposes of illustration only, a measuring band 601 has been partially disassembled from the adjustment mechanism that is driven via the bendable rod 48. These figures to not show a configuration obtained by the measuring band 601 during actual use of the sizing device. As shown in FIGS. 8, 9, the adjustment mechanism includes a cylindrical holder 602, the measuring band 601, and a hub member 603. As shown, the cylindrical holder 602, which has a proximal end 604 and a distal end 605, is structurally separate from the modular distal shaft 40, and is—instead—coupled thereto. In such embodiments, the proximal end 604 of the cylindrical holder 602 is adapted to couple to a distal end of the modular distal shaft 40, such as for example by use of an interference fit therewith, e.g. with the hub portion 405. The hub member 603 is, on its hand, rotationally coupled to the bendable rod 48.

The cylindrical holder 602 includes an opening or slot 606 extending longitudinally through a portion thereof. In some embodiments, the slot 606 extends along the entire length of the holder 602 from the proximal end 604 to the distal end 605. Adjacent the slot 606 is a coupling edge 607. As shown, the holder 602 also includes an annular lip 608 located at the distal end 605. In other embodiments, the holder 602 includes an annular lip at the proximal end 604 as well. The cylindrical holder 602 defines an internal, central chamber or bore 609.

As shown in FIGS. 8, 9, the measuring band 601 includes an elongated portion extending from a proximal end 610 to a distal end 611. The proximal end 610 is coupled to the holder 602 at or near the coupling edge 607. The distal end 611 of the measuring band 601 is coupled to the hub member 603. As shown, the hub member 603 includes a protrusion 612 defining an internal engagement portion 613 (shaped as a quadrangular recess or hole). The protrusion 612 and engagement portion 613 facilitate coupling of the hub member 603 to the bendable rod 48. Specifically, coupling may occur via one of shape coupling, interference fitting or snap-fit coupling. Shape coupling may occur e.g. by deforming the end of the bendable rod 48 intended to be coupled to the hub member 603 into a quadrangular tubular shape complementary to that of the engagement portion 603, then inserting the same into the engagement portion 603. Alternatively, shape coupling may be achieved by coupling a quadrangular section pin to the end of the bendable rod 48, then inserting (with axial and preferably radial play as well) the pin into the engagement portion 603 for torque transmission thereto. Interference fitting may be achieved e.g. by shaping the engagement portion as a circular recess or hole and sizing the same so as to achieve a desired interference with the bendable rod 48. Snap fit coupling may be achieved e.g. by notch-bulges pairs, wherein notches or openings provided on the surface of the bendable rod 48 at the end to be coupled to the engagement portion 613 are configured to snap fit with complementary and corresponding bulges on the inner surface of the engagement portion 613.

The measuring band 601 may be made from any material having suitable physical characteristics. In various embodiments, the band 601 is made from a biocompatible polymeric or metallic material. In embodiments where the band 601 is self-expandable, the band is made from a polymer or metal having shape memory and/or superelastic properties. Once such class of superelastic materials well known in the art are nickel-titanium alloys, such as nitinol. According to one exemplary embodiment, the measuring band has a length of between about 150 and 190 mm, a height of between about 1 and 10 mm, and a thickness of about 0.05 and 2 mm. In other embodiments, the measuring band may include other dimensions as appropriate for use of the band in measuring the circumference of a valve annulus.

In some embodiments, the measuring band 601 includes a longitudinally extending radiopaque portion to facilitate visualization of the measuring band during use of the device. In other embodiments, the longitudinally extending edge (or edges) of the measuring band 601 are tapered or otherwise softened, to help minimize trauma to the valve annulus or adjacent tissue during a sizing procedure.

According to various embodiments the hub member 603 and the measuring band 601 are removable from the holder 602. In these embodiments, the measuring band 601 and hub member 603 of the sizing device are readily disposable after use, while the remaining portions of the device may be sterilized and reused by the physician. In these embodiment, for example, the measuring band can be removed by unwinding and expanding the measuring band and then manipulating the measuring band around the distal annular lip 608. The measuring band 601 and hub 603 can then be slid distally out of the holder 602 for disposal. A new, sterile measuring band 601 and hub 603 can then be inserted into the holder 602, and the engagement portion 613 coupled to the bendable rod 48. In these embodiments, interference fitting between the bendable rod 48 and the engagement portion 613 may not be in general a preferred option.

Figure 10:
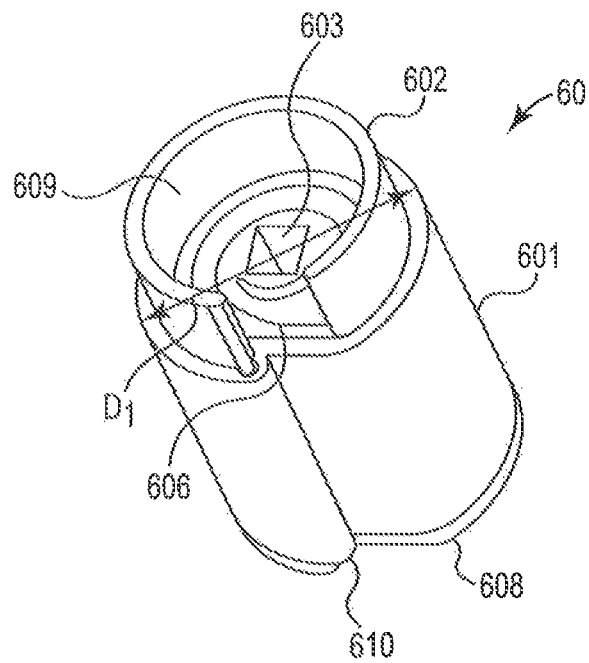
FIG. 10 is a diagram illustrating the sizing device in an assembled, collapsed configuration, in accordance with various embodiments of the disclosure.

FIG. 10 shows the sizing device 60, and particularly the adjustment mechanism thereof, in an assembled, collapsed configuration. For illustration purposes only, the cylindrical holder 602 is shown separated from the modular distal shaft 40. As shown in FIG. 10, the measuring band 601 is wound about the holder 602 in a clockwise direction, such that it extends along an outer surface of the holder 602, extends through the slot 606, and extends along an internal surface of the holder 602 in the central chamber 609. The proximal end 610 of the measuring band 601 is attached at or near the coupling edge of the holder 602, and the distal end 611 of the measuring band is coupled to the hub 603. In this configuration, the measuring band has a minimal effective diameter ($D_1$), which facilitates access to the valve annulus using standard minimally invasive access techniques and instruments. In the embodiment shown, the annular lip 608 extends radially outward from the holder a distance about equal to the thickness of the measuring band 601. In this embodiment, the leading (distal) edge of the measuring band is thus covered or protected by the annular lip 608. As shown in FIG. 10, in the assembled configuration, the hub member 603 is located inside the central chamber 609, with portions of the measuring band 601 wound thereabout.

Figure 11:
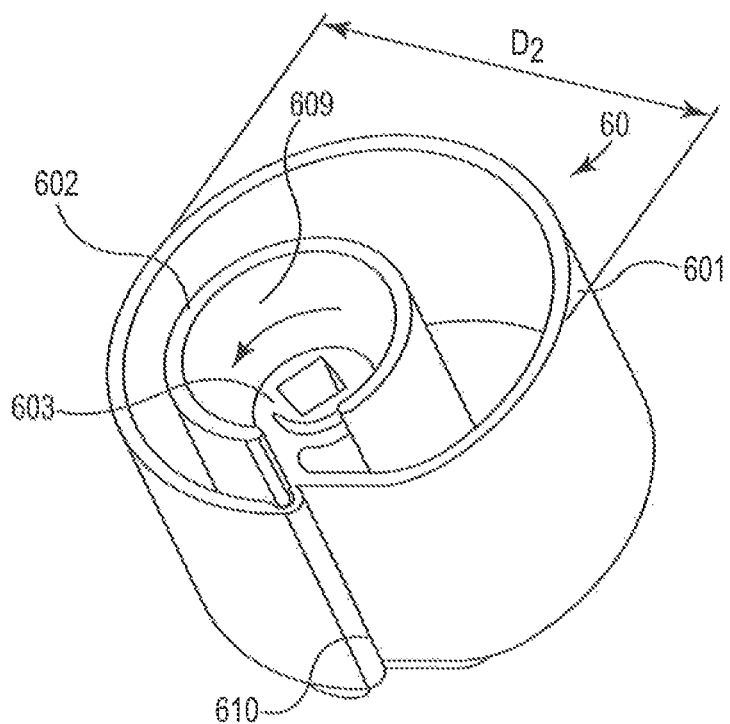
FIG. 11 is a diagram illustrating the sizing device in an assembled, expanded configuration, in accordance with various embodiments of the disclosure.

FIG. 11 shows the sizing device 60, and particularly the adjustment mechanism thereof, in an assembled, expanded configuration. Again, for illustration purposes, the cylindrical holder 602 is shown separated from the modular distal shaft 40. As shown, in the expanded configuration, the measuring band 601 is at least partially unwound, which results in an the measuring band 602 defining an expanded effective diameter ($D_2$). As shown, the proximal portion 610 of the measuring band 601 remains attached to the holder 602, and the distal portion 611 remains attached to the hub member 603. The hub member 603, however, has rotated in the direction indicated by the arrow in FIG. 11, to unwind the measuring band 601 and allow the same to extend out through the slot 606 and away from the holder 602. The effective length (i.e., the length extending out from the holder 602) corresponds to an amount of rotation of the central hub 603. As the hub rotates in a counter-clockwise direction driven by the rod 48, the measuring band 601 expands outwardly from the holder 602, and as the hub 603 rotates in a clockwise direction driven—again—by the rod 48, the measuring band 601 contracts towards the holder 602. In the most expanded configuration, the hub member 603 remains inside the holder 602, but all or nearly all portions of the measuring band 601 have extended out through the slot 607.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The following is claimed:

1. A bendable medical instrument comprising:
a handle at a proximal end of the bendable medical instrument;
a modular distal shaft including a plurality of vertebrae configured to bend and situated near a distal end of the bendable medical instrument, wherein each vertebra has a rhomboidal shape including a major dimension and a minor dimension;
a bendable internal rod operatively coupled to the handle and disposed through at least some of the plurality of vertebrae, the bendable internal rod having a modular cell structure and configured to be rotated relative to the modular distal shaft via actuation at the handle; and
a distal tip coupled to the modular distal shaft at the distal end, wherein the plurality of vertebrae are configured to bend to position the distal tip in a patient and the bendable internal rod is configured to bend with the plurality of vertebrae.

2. The instrument of claim 1, comprising at least one guide wire coupled to at least one of the handle and the modular distal shaft and operatively coupled to the plurality of vertebrae.

3. The instrument of claim 1, wherein each of the plurality of vertebrae has at least one guide hole configured to allow a guide wire to extend through the guide hole.

4. The instrument of claim 1, wherein the handle comprises a deployable component control knob configured to control a deployable component at the distal end.

5. The instrument of claim 1, wherein the distal tip comprises a deployable component and the handle comprises a deployable component control knob configured to provide at least one of control over a degree of deployment of the deployable component and measuring of the degree of deployment of the deployable component.

6. The instrument of claim 5, wherein the deployable component includes a valve annulus sizing device comprising:
a holder having a proximal end and a distal end, the proximal end of the holder being coupled to the modular distal shaft,
a hub member rotationally coupled to the bendable internal rod and rotatably mounted into a central chamber of the holder,
a measuring band having a proximal end and a distal end, the proximal end being coupled to the holder, and the distal end being coupled to the hub member,
wherein the measuring band is wound about the holder and extends through a slot of the holder to the hub member.

7. The instrument of claim 6, wherein the measuring band includes:
a collapsed configuration wherein it is wound about the holder such that it extends along an outer surface of the holder, extends through the slot, and along an internal surface of the holder in the central chamber, and
an expanded configuration wherein the measuring band is at least partially unwound to extend out through the slot and away from the holder.

8. The instrument of claim 1, wherein the bendable internal rod is configured to transmit torque from the proximal end to the distal end.

9. The instrument of claim 8, wherein the bendable internal rod has a dovetail cell structure.

10. The instrument of claim 1, wherein the bendable internal rod is bendable in four directions.

11. The instrument of claim 1, wherein each of the plurality of vertebrae defines a central hole configured to allow the bendable internal rod to extend through the central hole.

12. The instrument of claim 1, wherein the modular distal shaft is bendable in four directions.

13. The instrument of claim 1, wherein each of the plurality of vertebrae has a blocking protrusion configured to disable relative rotational movement between the plurality of vertebrae.

14. The instrument of claim 1, wherein each of the plurality of vertebrae has at least one alignment protrusion on a front side and at least one alignment groove on a back side to couple and align the plurality of vertebrae into the modular distal shaft.

15. The instrument of claim 1, wherein each vertebra has two guide holes configured to allow a guidewire to extend through the guide hole, wherein each guidewire is plastically deformable and configured to maintain the shape imparted thereto upon deformation.

16. The instrument of claim 15, wherein each guidewire includes a first end and a second end fixed, respectively, to a first terminal member and a second terminal member arranged at opposite ends of the plurality of vertebrae.

17. The instrument of claim 16, wherein the first end and the second end of each guidewire are curved.

18. The instrument of claim 15, wherein the two guide holes are arranged along the major dimension.

19. A bendable medical instrument comprising:
a handle at a proximal end of the bendable medical instrument;
a modular distal shaft situated near a distal end of the bendable medical instrument, the modular distal shaft including a plurality of vertebrae axially aligned and configured to provide bendability to the modular distal shaft, each of the plurality of vertebrae having at least one guide hole and a rhomboidal shape including a major dimension and a minor dimension;
at least one guide wire coupled to the handle and inserted through the at least one guide hole in each of the plurality of vertebrae;
a rod including a plurality of cells axially aligned and configured to provide bendability to the rod, the rod coupled to the handle and disposed through each of the plurality of vertebrae; and
a distal tip coupled to the modular distal shaft at the distal end, wherein the plurality of vertebrae are configured to bend and the rod is configured to bend inside the plurality of vertebrae.

20. The instrument of claim 19, wherein the handle comprises a deployable component control knob configured to control a deployable component at the distal end.

21. The instrument of claim 19, wherein each of the plurality of cells has a dovetail cell structure.

22. The instrument of claim 19, wherein:
the distal tip includes a deployable component coupled to the rod; and
the handle includes a deployable component control knob coupled to the rod to control deployment of the deployable component.

23. A method of manipulating a position of a deployable component situated at a distal end of a bendable medical instrument having a handle, the method comprising:
bending a plurality of vertebrae in a modular distal shaft that is coupled to the deployable component and situated near the deployable component, each of the plurality of vertebrae having at least one guide hole, at least one guide wire inserted through the at least one guide hole, and a rhomboidal shape including a major dimension and a minor dimension; and
bending a plurality of cells of a bendable internal rod coupled to the handle and disposed through each of the plurality of vertebrae.

24. The method of claim 23, wherein bending a plurality of vertebrae and bending a plurality of cells comprises simultaneously bending the plurality of vertebrae and the plurality of cells.

25. The method of claim 23, wherein bending a plurality of vertebrae comprises manually bending the plurality of vertebrae.

26. The method of claim 23, wherein bending a plurality of cells comprises manually bending the plurality of cells.

* * * * *